United States Patent [19]

Haas et al.

[11] 4,297,358
[45] Oct. 27, 1981

[54] NOVEL 4,7-PHENANTHROLINE DERIVATIVES AND PHARMACEUTICAL COMPOSITIONS CONTAINING THEM AND THEIR USE

[75] Inventors: Georges Haas, Binningen; Knut A. Jaeggi, Basel; Alberto Rossi, Oberwil; Alex Sele, Muttenz, all of Switzerland

[73] Assignee: Ciba-Geigy Corporation, Ardsley, N.Y.

[21] Appl. No.: 109,715

[22] Filed: Jan. 4, 1980

[30] Foreign Application Priority Data

Jan. 16, 1979 [CH] Switzerland .............................. 402/79

[51] Int. Cl.³ .................. C07D 487/04; A61K 31/435
[52] U.S. Cl. ....................................... 424/256; 546/88
[58] Field of Search ............................ 546/88; 424/256

[56] References Cited

U.S. PATENT DOCUMENTS 3,313,817  4/1967  Lesher et al. ........................ 546/88
3,790,577  2/1974  Waring .......................... 260/287 R

OTHER PUBLICATIONS

Lesher, Chem. Abstracts, vol. 67, No. 21, 100, 129a, Nov. 20, 1967.

Primary Examiner—Alan L. Rotman
Attorney, Agent, or Firm—Prabodh I. Almaula

[57] ABSTRACT

New 4,7-phenanthroline derivatives of the formula (I)

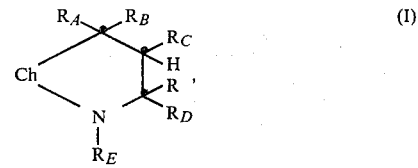

in which
Ch represents an optionally substituted 5,6-quinolinylene radical of which the 6-position is joined to the —N($R_E$)— group, and
R represents an optionally esterified or amidated carboxy group,
and in which either
$R_A$ and $R_B$ together represent oxo,
$R_C$ and $R_D$ together represent an additional link, and
$R_E$ represents a radical $R_1$ which is hydrogen, or an aliphatic, cycloaliphatic, araliphatic or heterocyclic-aliphatic radical, or
$R_A$ represents an optionally etherified hydroxy group and
$R_B$ together with $R_C$ and $R_D$ together with $R_E$ in each case represents an additional link, and salts of salt-forming compounds of the formula (I), compounds of the formula (I) or the salts thereof have anti-allergic properties. They can be prepared in accordance with processes known per se and may be used as active substances in pharmaceutical preparations.

13 Claims, No Drawings

NOVEL 4,7-PHENANTHROLINE DERIVATIVES AND PHARMACEUTICAL COMPOSITIONS CONTAINING THEM AND THEIR USE

The invention relates to new 4,7-phenanthroline derivatives of the general formula (I)

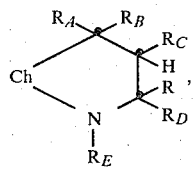

in which
Ch represents an optionally substituted 5,6-quinolinylene radical of which the 6-position is joined to the —N($R_E$)— group, and
R represents an optionally esterified or amidated carboxy group,
and in which either
$R_A$ and $R_B$ together represent oxo,
$R_C$ and $R_D$ together represent an additional link, and
$R_E$ represents a radical $R_1$, which is hydrogen or an aliphatic, cycloaliphatic, araliphatic or heterocyclic-aliphatic radical, or
$R_A$ represents an optionally etherified hydroxy group and
$R_B$ together with $R_C$, and $R_D$ together with $R_E$, in each case represents an additional link,
and salts of salt-forming compounds of the formula (I), pharmaceutical preparations containing compounds of the formula (I) or the salts thereof and the use of compounds of the formula (I) and the salts thereof.

Aliphatic, cycloaliphatic, and araliphatic radicals are especially optionally substituted aliphatic, cycloaliphatic or araliphatic hydrocarbon radicals, such as a corresponding lower alkyl, lower alkenyl, cycloalkyl or phenyl-lower alkyl radical. Substituents are, for example, hydroxy and/or lower alkoxy, lower alkylthio or phenylthio, lower alkanesulphinyl or benzenesulphinyl or lower alkanesulphonyl or benzenesulphonyl or di-lower alkylamino or lower alkyleneamino or aza-lower alkyleneamino, oxa-lower alkyleneamino or thia-lower alkyleneamino having from 5 to 7 ring members. Substituted hydrocarbon radicals of this kind are especially hydroxy-lower alkyl, lower alkoxy-lower alkyl and di-lower alkylamino-lower alkyl radicals, and also 5- to 7-membered lower alkyleneamino-lower alkyl or aza, oxa- or thia-lower alkyleneamino-lower alkyl radicals. Heterocyclyl in heterocyclic or heterocyclic-aliphatic radicals is especially monocyclic hererocyclyl of an aromatic nature having one hetero atom, such as oxygen, sulphur or nitrogen, as the ring member, such as furyl, thienyl or pyridyl. In heterocyclic-aliphatic radicals the aliphatic moiety is, for example, a suitable aliphatic hydrocarbon radical, especially lower alkyl.

Possible additional substituents of Ch are, for example, lower alkyl, lower alkoxy, trifluoromethyl, hydroxy and/or halogen, wherein one or more substituents may be present.

Esterified carboxy is, for example, carboxy esterified with an aliphatic or araliphatic alcohol, such as an optionally substituted aliphatic or araliphatic alcohol, for example suitable lower alkoxycarbonyl or phenyl-lower alkoxycarbonyl. Substituted lower alkoxycarbonyl is, for example, hydroxy-lower alkoxycarbonyl, lower alkoxy lower alkoxycarbonyl, di-lower alkylamino-lower alkoxycarbonyl, or lower alkyleneamino-lower alkoxycarbonyl, aza-lower alkyleneamino-lower alkoxycarbonyl, oxa-lower alkyleneamino-lower alkoxycarbonyl or thia-lower alkyleneamino-lower alkoxycarbonyl. Substituents of phenyl-lower alkoxycarbonyl are, for example, lower alkyl, lower alkoxy and/or halogen.

In amidated carboxy, the amino group represents, for example, amino optionally mono-substituted by hydroxy or mono- or di-substituted by aliphatic radicals, such as amino, hydroxyamino, mono-lower alkylamino, di-lower alkylamino, lower alkyleneamino, or aza-lower alkyleneamino, oxo-lower alkyleneamino or thia-lower alkyleneamino each having 5 to 7 ring members.

Etherified hydroxy is, for example, lower alkoxy, lower alkenyloxy, lower alkoxy-lower alkoxy, di-lower alkylamino-lower alkoxy or 5- to 7-membered lower alkyleneamino-lower alkoxy, aza-lower alkyleneamino-lower alkoxy, oxa-lower alkyleneamino-lower alkoxy or thia-lower alkyleneamino-lower alkoxy.

Hereinbefore and hereinafter "lower" organic radicals and compounds shall be preferably understood to be those having 7 and up to 7 carbon atoms, and especially those having 4 and up to 4 carbon atoms.

Lower alkyl is, for example, methyl, ethyl, propyl, isopropyl, butyl, isobutyl, secondary butyl, tertiary butyl, pentyl, hexyl or heptyl.

Lower alkenyl is, for example, vinyl, 1-methylvinyl, 1-ethylvinyl, allyl or 2- or 3-methallyl.

Lower alkoxy and lower alkoxy in lower alkoxycarbonyl is, for example, methoxy, ethoxy, propoxy, isopropoxy, butoxy, isobutoxy, secondary butoxy, tertiary butoxy, pentyloxy, hexyloxy or heptyloxy. Lower alkylthio is, for example, methylthio, ethylthio, propylthio, butylthio, pentylthio, hexylthio or heptylthio.

Hydroxy-lower alkyl is especially 2- and/or 3-hydroxy-lower alkyl, for example 2-hydroxyethyl, 3-hydroxypropyl or 2,3-dihydroxypropyl. Correspondingly, hydroxy-lower alkoxy and hydroxy-lower alkoxy in hydroxy-lower alkoxycarbonyl is especially 2- and/or 3-hydroxy-lower alkoxy, for example 2-hydroxyethoxy, 3-hydroxypropoxy or 2,3-dihydroxypropoxy.

Lower alkoxy-lower alkyl is especially 2- and/or 3-lower alkoxy-lower alkyl, for example 2-methoxyethyl, 2-ethoxyethyl or 3-methoxypropyl. Correspondingly, lower alkoxy-lower alkoxy and lower alkoxy-lower alkoxy in lower alkoxy-lower alkoxycarbonyl is especially 2-and/or 3-lower alkoxy-lower alkoxy, for example 2-methoxyethoxy, 2-ethoxyethoxy or 3-methoxypropoxy.

Di-lower alkylamino-lower alkyl is especially 2- and/or 3-di-lower alkylamino-lower alkyl, for example 2-dimethylaminoethyl, 2-diethylaminoethyl or 3-dimethylaminopropyl. Correspondingly, di-lower alkylamino-lower alkoxy and di-lower alkylamino-lower alkoxy in di-lower alkylamino-lower alkoxycarbonyl is especially 2-and/or 3di-lower alkylamino-lower alkoxy, for example 2-dimethylaminoethoxy, 2-diethylaminoethoxy or 3-dimethylaminopropoxy. 5- to 7-membered lower alkyleneamino-lower alkyl or aza, oxo- or thia-lower alkyleneamino-lower alkyl is, for example, pyrrolidino-, piperidino-, morpholino-, thiamorpholino-, piperazino- or N'-lower alkylpiperazino-lower alkyl.

Phenyl-lower alkyl is, for example, benzyl, or 1- or 2-phenylethyl, and phenyl-lower alkoxy and phenyl-lower alkoxy in phenyl-lower alkoxycarbonyl is, for example, benzyloxy, or 1- or 2-phenylethoxy.

Cycloalkyl is especially cycloalkyl having 3 to 8, and especially 5 to 7, ring members, for example cyclopentyl, cyclohexyl or cycloheptyl, or also cyclopropyl, cyclobutyl or cyclooctyl.

Furyl-lower alkyl, thienyl-lower alkyl, or pyridyl-lower alkyl has as the alkyl moiety especially methyl, and is, for example, furfuryl, 2-thenyl, or pyridylmethyl, such as pyrid-2-ylmethyl or pyrid-4-ylmethyl.

Mono- or di-lower alkylamino is, for example, methylamino, dimethylamino, ethylamino, diethylamino, propylamino or butylamino.

Lower-alkyleneamino and aza, oxa- or thia-lower alkyleneamino and also the same in correspondingly substituted lower alkyl and lower alkoxy radicals represent, for example, pyrrolidino, piperidino, morpholino, thiamorpholino, or N'-lower alkylpiperazino, such as N'-methylpiperazino.

Halogen is especially halogen of an atomic number up to and including 35, such as fluorine, chlorine or bromine.

Salt-forming compounds of the formula (I) are, for example, acid compounds of the formula (I) containing carboxy R and/or enolic hydroxy groups, for example hydroxy $R_A$, or basic compounds of the formula (I) containing basic groups. Salts thereof are, for example, salts of acidic compounds with bases, especially with pharmaceutically suitable bases, such as alkali metal or alkaline earth metal salts, for example sodium, potassium, magnesium or calcium salts, and ammonium salts with ammonia or amines, such as lower alkylamines or hydroxy-lower alkylamines, for example trimethylamine, triethylamine or di- or tri(2-hydroxyethyl)amine; or acid addition salts, especially with pharmaceutically suitable acids, such as mineral acids, for example hydrohalic acids, sulphuric acid or phosphoric acid, or with suitable organic sulphonic or carboxylic acids, for example hydrochlorides, hydrobromides, sulphates, phosphates, malates, maleates, fumarates or tartrates.

The invention relates especially to compounds of the formula (I) in which Ch represents 5,6-quinolinylene optionally additionally substituted by lower alkyl, lower alkoxy, hydroxy and/or halogen, R represents carboxy, lower alkoxycarbonyl, hydroxy-lower alkoxycarbonyl, lower alkoxy-lower alkoxycarbonyl, di-lower alkylamino-lower alkoxycarbonyl, 5- to 7-membered lower alkyleneamino lower alkoxycarbonyl or aza, oxa- or thia-lower alkyleneamino lower alkoxycarbonyl, or amidated carboxy, which contains as amino group amino, hydroxyamino, lower alkylamino, di-lower alkylamino, 5- to 7-membered lower alkyleneamido, or aza-, oxa- or thia-lower alkyleneamino, and in which either $R_A$ and $R_B$ together represent oxo, $R_C$ and $R_D$ together represent an additional link, and $R_E$ represents hydrogen, lower alkyl, hydroxy-lower alkyl, lower alkoxy-lower alkyl, di-lower alkylamino-lower alkyl, 5- to 7-membered lower alkyleneamino lower alkyl, aza-, oxa- or thia-lower alkyleneamino-lower alkyl, lower alkenyl, cycloalkyl having 3 to 8, especially 5 to 7, ring members, or phenyl-lower alkyl, furyl-lower alkyl, thienyl-lower alkyl or pyridyl-lower alkyl optionally substituted by lower alkyl, lower alkoxy, and/or halogen, or $R_A$ represents hydroxy, lower alkoxy, or lower alkenyloxy and $R_B$ together with $R_C$, and $R_D$ together with $R_E$ in each case represents an additional link, and salts of the above-defined compounds having salt-forming properties.

The invention relates especially firstly to compounds of the formula (Ia)

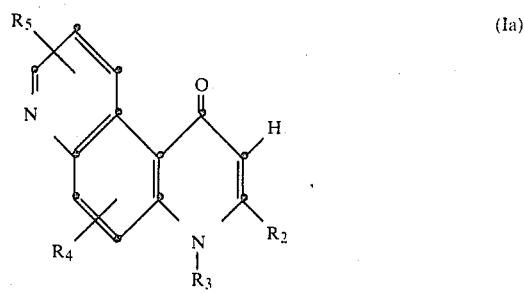

(Ia)

and, secondly, to compounds of the formula (Ib)

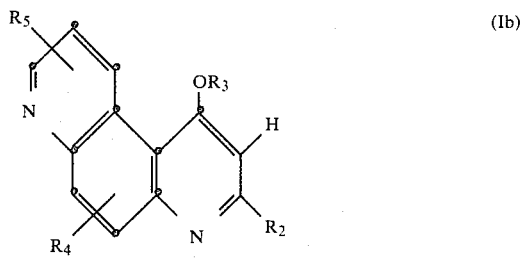

(Ib)

in which $R_2$ represents carboxy; lower alkoxycarbonyl having up to 5 carbon atoms, for example methoxycarbonyl or ethoxycarbonyl; hydroxy-lower alkoxycarbonyl having up to 5 carbon atoms, for example 2-hydroxyethycarbonyl; lower alkoxy-lower alkoxycarbonyl having up to 4 carbon atoms in each of the alkyl moieties, for example, 2-methoxyethoxycarbonyl or 2-ethoxyethoxycarbonyl; di-lower alkylamino-lower alkoxycarbonyl having up to 4 carbon atoms in each of the alkyl and alkoxy moieties, for example 2-dimethylaminoethoxycarbonyl or 2-diethylaminoethoxycarbonyl; carbamoyl; N-hydroxycarbamoyl; or N-lower alkylcarbamoyl or N,N-di-lower alkylcarbamoyl having up to 4 carbon atoms in each alkyl moiety, for example N-methylcarbamoyl, N-ethylcarbamoyl or N,N-dimethylcarbamoyl, $R_3$ represents hydrogen, lower alkyl having up to 4 carbon atoms, for example methyl; lower alkenyl having up to 4 carbon atoms; phenyl-lower alkyl, furyl-lower alkyl, thienyl-lower alkyl or pyridyl-lower alkyl having up to 4 carbon atoms in each alkyl moiety and optionally substituted by lower alkyl having up to 4 carbon atoms, for example, methyl, by lower alkoxy having up to 4 carbon atoms, for example methoxy, and/or by halogen of an atomic number up to and including 35, for example chlorine, for example corresponding benzyl, 1- or 2-phenylethyl, furfuryl, 2-thenyl or 2- or 4-picolyl; lower alkoxy-lower alkyl having up to 4 carbon atoms in each of the alkoxy and alkyl moieties, for example 2-methoxyethyl or 2-ethoxyethyl; or di-lower alkylamino-lower alkyl, lower alkyleneamino-lower alkyl or aza-, thia- or oxa-lower alkyleneamino-lower alkyl, in which lower alkyl has up to 4 carbon atoms and lower alkylene or aza-, oxa- or thia-lower alkylene has 5–7 ring members, for example 2-dimethylaminoethyl, 2- diethylaminoethyl, 2-pyrrolidinoethyl, 2-piperidinoethyl, 2-morpholinoethyl, 2-thiamorpholinoethyl, 2-piperazinoethyl or 2-(4-methylpiperazino)ethyl, and R₄ and R₅, independently of one another, each represents hydrogen; lower alkyl having up to 4 carbon atoms, for example methyl; lower alkoxy having up to 4 carbon atoms, for example methoxy; hydroxy; or halogen of an atomic number up to and including 35, for example chlorine, and salts of salt-forming compounds of the formulae Ia and Ib.

The invention relates more especially, firstly, to compounds of the formula (II)

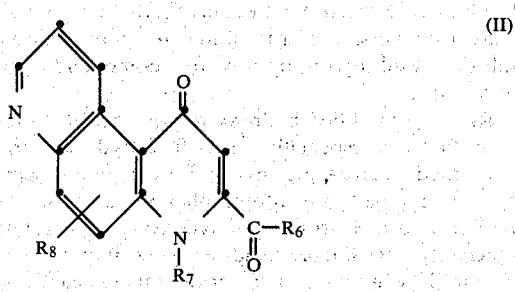

and, secondly, to compounds of the formula (III)

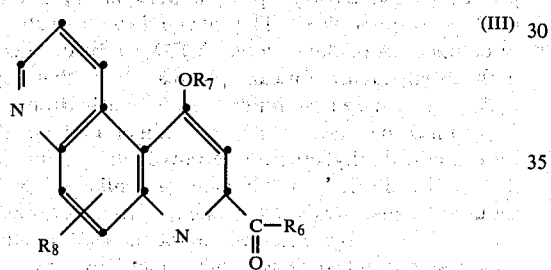

in which
R₆ represents hydroxy or especially lower alkoxy having up to 4 carbon atoms, for example, methoxy, ethoxy, propoxy or butoxy,
R₇ represents hydrogen, or lower alkyl having up to 4 carbon atoms, for example methyl or ethyl, and
R₈ represents hydrogen or especially lower alkoxy having up to 4 carbon atoms, for example methoxy or ethoxy, and salts of salt-forming compounds of the formulae II and III.

The invention relates namely to the compounds of the formula (I) mentioned in the Examples.

The compounds of the formula (I) may be prepared in accordance with methods known per se, for example by intramolecular cyclisation of a compound of the formula (IV)

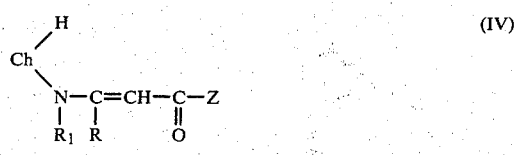

in which
Z represents a radical capable of being split off, or a salt thereof, and, if desired, conversion of the resulting compound into a different compound of the formula (I), and/or conversion of a resulting free compound into a salt or a resulting salt into the free compound or into a different salt.

The radical Z capable of being split off is, for example, an optionally etherified or esterified hydroxy group. Etherified hydroxy groups are, for example, hydroxy groups etherified with aliphatic, araliphatic or aromatic alcohols, such as lower alkoxy groups, for example methoxy or ethoxy groups, or optionally substituted phenoxy, such as phenoxy substituted by lower alkyl, lower alkoxy or especially halogen and/or nitro, for example phenoxy, 4-chlorophenoxy, 4-nitrophenoxy, 2,4-dinitrophenoxy and 3,5-dichlorophenoxy. Esterified hydroxy groups are, for example, hydroxy groups esterified with organic carboxylic acids, such as lower alkanoic acids, or with mono-functional carbonic acid derivatives, such as carbonic acid monoesters or monohalides, and especially with mineral acids such as hydrohalic acids, for example formyloxy, acetoxy, chlorocarbonyloxy, lower-alkoxycarbonyloxy, such as ethoxycarbonyloxy, and especially halogen atoms, such as chlorine, bromine or iodine; and also sulphonyloxy groups, such as sulphonyloxy groups derived from organic sulphonic acids or halosulphonic acids, for example fluorosulphonyloxy, chlorosulphonyloxy, methanesulphonyloxy, benzenesulphonyloxy, p-toluenesulphonyloxy or p-bromosulphonyloxy. Salts of compounds of the formula (IV) are especially salts with bases, such as alkali metal salts, of compounds of the formula (IV) in which Z is hydroxy and/or R is carboxy, or acid addition salts of basic compounds of the formula (IV).

The intramolecular condensation may be carried out in the usual manner, preferably by heating, for example to approximately 150° C. to approximately 250° C., if required in the presence of a solvent that is inert under the reaction conditions, and/or in the presence of a suitable condensing agent, if necessary under an inert gas, such as nitrogen, and/or in a closed vessel.

Solvents that are inert under the reaction conditions are, for example, higher-boiling hydrocarbons, such as toluene or xylene, ethers such as diphenyl ether, or tertiary carboxylic acid amides, such as dimethylformamide or N-methylpyrrolidone. Suitable condensing agents are, for example, acidic agents, such as protonic acids, for example mineral acids, inter alia sulphuric acid, phosphoric acid or polyphosphoric acid; or acidic mineral acid esters, such as mono- or di-lower alkylphosphates or phosphites, inter alia triethyl phosphate, triethylphosphite or tetraethylpyrophosphate; and also Lewis acids, such as, for example, aluminium chloride, aluminium bromide, zinc chloride, borontrifluoride or antimony pentachloride.

The starting substances of the formula (IV) may be obtained by methods known per se, using, for example, suitable 6-aminoquinolines as starting substances; for the preparation of starting substances of the formula (IV), in which Z represents an etherified hydroxy group, for example, the 6-aminoquinoline compound is condensed in the usual manner with an acetylenedicarboxylic acid derivative of the formula R—C≡C—C(=O)—Z (V), for example an acetylenecarboxylic acid diester, such as an acetylenedicarboxylic acid di-lower alkyl ester, or with a different suitable aliphatic 1,4-dicarboxylic acid derivative, for example chlorofumaric acid or oxalacetic acid, or with a diester, ester halide or dihalide thereof, and, if desired, a resulting ester is hydrolysed to form an acid, and/or a resulting acid is converted into a different functional derivative. Thus, for example, in the manner of a Conrad-Limpach reaction, the reaction can be carried out in an aromatic or aliphatic hydrocarbon, for example in benzene or toluene, with an oxalacetic acid mono- or di-lower alkyl ester, the reaction preferably being carried out at elevated temperature, for example at 50° to 150° C., especially at 80° to 110° C., and advantageously with removal of the water of reaction by azeotropic distillation. Alternatively, the reaction can be carried out in known manner, for example in the presence of a basic condensing agent, such as aqueous sodium or potassium hydroxide solution, pyridine or triethylamine, with an oxalacetic acid ethyl ester chloride or mono-chloride or, preferably, in an alkanol, such as methanol, with an acetylenedicarboxylic acid di-lower alkyl ester, for example acetylenedicarboxylic acid dimethyl ester.

The compounds of the formula (I) can furthermore be prepared by intramolecular cyclisation of a compound of the formula (VI)

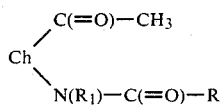  (VI)

or a salt thereof and, if desired, conversion of the resulting compound into a different compound of the formula (I) and/or conversion of a resulting free compound into a salt, or conversion of a resulting salt into the free compound or into a different salt.

The intramolecular cyclisation is carried out in the usual manner, preferably in a substantially anhydrous solvent, advantageously in the presence of a dehydrating agent, and, if required, in the presence of a basic condensing agent, if necessary at elevated temperature, for example at approximately 50° to 150° C., under an inert gas, such as nitrogen, and/or in a closed vessel. Suitable solvents are, especially, lower alkanols, such as methanol, ethanol or butanol, lower ethylene glycols, such as ethyleneglycol, and also dimethyl sulphoxide, dimethylformamide, diphenyl ether and high-boiling hydrocarbons, such as xylenes. Basic condensing agents are, for example, alkali metal alcoholates, such as alkali metal lower alkanolates, for example sodium methylate, sodium ethylate or sodium tert.-butylate, or alkali metal hydrides, such as sodium hydride.

The starting substances of formula (VI) can be prepared in accordance with methods known per se, for example by reacting a suitable 5-acetyl-6-aminoquinoline with a compound of the formula

R—COOH    (VII)

or with a reactive functional derivative thereof, such as an ester, for example a di-lower alkyl ester, or ester halide, for example a lower alkyl ester chloride and, if desired, converting R in the resulting compound of the formula (VI) into a different group R in the usual manner.

The compounds of the formula (I) can furthermore be prepared by intramolecular cyclisation of a compound of the formula (VIII)

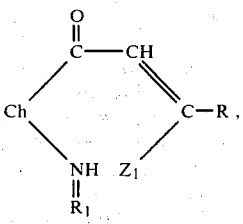  (VIII)

in which $Z_1$ is an optionally reactive modified hydroxy group, or a tautomer thereof and/or a salt thereof, and, if desired, conversion of a compound which may thus be obtained into a different compound of the formula (I) and/or conversion of a resulting free compound into a salt or a resulting salt into the free compound or into a different salt.

Reactive modified hydroxy groups are, for example, etherified or, especially, esterified hydroxy groups. Etherified hydroxy groups are, for example, lower alkoxy or optionally substituted phenoxy groups, and esterified hydroxy groups are hydroxy groups esterified especially with mineral acids, such as hydrohalic acids or with halosulphonic acids or organic sulphonic acids, such as halogen, for example chlorine, bromine or iodine, or methanesulphonyloxy, benzenesulphonyloxy, p-toluenesulphonyloxy, p-bromobenzenesulphonyloxy or fluorosulphonyloxy. The intramolecular cyclisation of compounds of the formula (VIII) can be carried out in the usual manner, for example in a solvent that is inert under the reaction conditions, such as a hydrocarbon, for example benzene, toluene or a mineral oil, an ether, for example diethyl ether, or tetrahydrofuran, dimethylformamide, dimethyl sulphoxide, or similar solvents, if required whilst heating, for example to approximately 50° to 150° C., advantageously in the presence of a basic condensing agent, such as an alkali metal hydroxide, for example sodium or potassium hydroxide, or in the presence of an organic nitrogen base, for example pyridine or triethylamine, if necessary under an inert gas, such as nitrogen, and/or in a closed vessel.

The starting substances of the formula (VIII) can be prepared in accordance with methods known per se, for example by reacting a suitable 5-acetyl-6-aminoquinoline in the usual manner with a compound of the formula $Z_1$—C(=O)—R (IX), for example with a suitable oxalic acid ester chloride or oxalic acid diester, or by reacting a suitable 6-aminoquinolin-5-carboxylic acid or an ester thereof with a compound of the formula $CH_3$—C(=O)—R (X), and, if desired, converting the hydroxy group $Z_1$ first formed in the resulting compound into a different group $Z_1$.

The compounds of the formula (I) can furthermore be prepared by converting the group R' in a compound of the formula (XI)

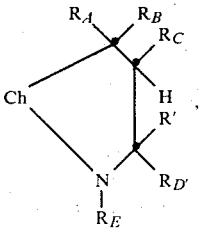  (XI)

in which R' is a radical that may be converted into an optionally esterified or amidated carboxy group R, or the group R' in a salt thereof, into the optionally esterified or amidated carboxy group R and, if desired, converting a resulting compound into a different compound of the formula (I) or converting a resulting salt-forming compound into a salt, or a resulting salt into the free compound or into a different salt.

Groups R' that can be converted into optionally esterified or amidated carboxy are, for example, functionally modified carboxy groups other than esterified or amidated carboxy R that may be converted by solvolysis into optionally esterified or amidated carboxy groups. Such groups are, for example, cyano, anhydridised carboxy groups, imino ether groups, imino ester groups and also etherified and/or esterified trihydroxymethyl groups. Anhydridised carboxy groups are, for example, carboxy groups anhydridised with a mineral acid, such as a hydrohalic acid, with a halosulphonic acid, such as fluorosulphonic acid, or with an organic sulphonic or carboxylic acid, such as an aliphatic or aromatic sulphonic or carboxylic acid. Imino ether groups are, for example, imino ether groups derived from esterified carboxy groups R, such as O-lower alkylcarbamoyl; or cyclic imino ether groups, such as 4,4- or 5,5-di-lower alkyl-4,5-dihydrooxazolyl-(2), for example 4,4- or 5,5-dimethyl-4,5-dihydrooxazolyl-(2), or 4,4,6-tri-lower alkyl-5,6-dihydrooxazinyl-(2), for example 4,4,6-trimethyl-5,6-dihydrooxazinyl-(2). Imino ester groups are, for example, imino ester groups derived from amidated carboxy groups R and esterified with hydrohalic acids or organic carboxylic acids, such as lower alkanoic acids, for example chlorocarbimino or O-lower alkanoylcarbamoyl. Etherified and/or esterified trihydroxymethyl groups are, for example, etherified trihydroxymethyl groups corresponding to esterified carboxy groups R and/or trihydroxymethyl groups esterified with mineral acids, such as hydrohalic acids, for example tri-lower alkoxymethyl, lower alkoxydihalomethyl or trihalomethyl, especially those in which halogen is chlorine or bromine. Other groups that can be converted by solvolysis into amidated carboxy groups R are, for example, dihalogenated carbamoyl groups corresponding to these, that is to say, corresponding amino-dihalomethyl groups, especially aminodichloromethyl groups.

The groups mentioned may be converted by customary hydrolysis into carboxy groups, imino ether groups and etherified hydroxydihalomethyl groups, such as lower alkoxydihalomethyl groups, and also into esterified carboxy groups, aminodihalomethyl groups can be converted into amidated carboxy groups, and cyano can be converted into unsubstituted carbamoyl groups. The hydrolysis is carried out in the usual manner, for example in the presence of an acidic or alkaline hydrolysing agent, usually in the presence of a solvent and/or diluent or a mixture thereof, and, if necessary, whilst cooling or heating, for example in a temperature range of from approximately 0° C. to approximately 120° C., if required under an inert gas, such as nitrogen, and/or in a closed vessel. Acidic hydrolysing agents are, for example, mineral acids, such hydrohalic acids, for example hydrochloric acid; oxyacids of sulphur or phosphorus, such as sulphuric or phosphoric acid; organic sulphonic acids, for example p-toluenesulphonic acid or methanesulphonic acid; or organic carboxylic acids, such as lower alkanecarboxylic acids, for example formic or acetic acid. Basic hydrolysing agents are, for example, alkali metal hydroxides, for example sodium or potassium hydroxide and alkali metal carbonates, for example sodium or potassium carbonate. Suitable solvents or diluents are preferably water-miscible solvents, such as lower alkanols, for example ethanol or methanol, lower ketones, for example acetone, or tertiary alkanoic acid amides, for example dimethylformamide or N-methylpyrrolidone.

Anhydridised carboxy groups and also cyclic imino ether groups may furthermore be converted into esterified carboxy groups R by alcoholysis, that is to say, reaction with a suitable alcohol. This reaction is carried out in the usual manner, when using anhydrides as starting materials for example in the presence of a basic condensing agent such as an alkali metal hydroxide or alkali metal carbonate, for example sodium or potassium hydroxide or corresponding carbonates, or in the presence of organic nitrogen bases, such as pyridine or triethylamine and, when using cyclic imino ethers as starting materials, preferably in anhydrous conditions, for example in the presence of hydrogen chloride, phosphoric acid, sulphuric acid or p-toluenesulphonic acid, if required whilst heating, for example in a temperature range of from approximately 0° C. to approximately 150° C., under an inert gas, such as nitrogen, and/or in a closed vessel.

Anhydridised carboxy groups may furthermore be converted into amidated carboxy groups R in the usual manner by ammonolysis or aminolysis, that is to say, reaction with ammonia or with a corresponding amine having at least one hydrogen atom.

Further radicals R' that can be converted into optionally esterified carboxy groups R are groups that can be converted into these by oxidation, such as the optionally hydrated formyl group which may be converted by oxidation into carboxy, or etherified hydroxymethyl groups which may be converted by oxidation into esterified carboxy groups.

The oxidation may be carried out in a manner known per se, for example by reaction with a heavy metal oxidising compound, preferably a compound containing chromium(VI) or manganese(VII), for example with chromium trioxide or especially potassium permanganate, or with compounds containing bismuth(III), manganese(IV) or silver(I), for example with bismuth oxide, manganese dioxide or silver oxide; or by atmospheric oxidation. This reaction is advantageously carried out in the presence of a solvent that is inert towards the reactants, for example acetone or pyridine, or in the presence of a mixture thereof, preferably an aqueous mixture thereof, if necessary whilst cooling or heating, for example in a temperature range of from approximately 0° C. to 80° C.

The starting substances of the formula (XI) may be prepared in accordance with methods known per se.

Compounds of the formula (XI) in which R' represents cyano, etherified hydroxymethyl or formyl, can be obtained, for example, by intramolecular condensation of suitable compounds of the formula

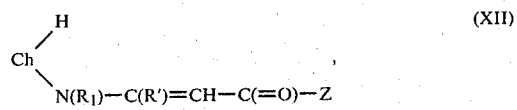

in which Z represents a reactive esterified hydroxy group or an etherified hydroxy group, for example halogen or lower alkoxy, such as methoxy, and in which a formyl group R' may also be present in a temporarily protected form, for example in an acetalysed or acylalised form, for example as di-lower alkoxymethyl, lower alkylenemethyl, dioxymethyl or dihalomethyl. The nitriles of the formula (XI) which may be obtained, for example, in this manner, can be converted into imino ethers of the formula (XI) by customary reaction, for example by acid-catalysed reaction, with the corresponding alcohols or amino alcohols, for example, into open-chained imino ethers by reaction with a lower alkanol, or into cyclic imino ethers by reaction with a suitable aminoalkanol or alkanediol, for example 4-amino-2-methylpentan-2-ol or 2-methylpentane-2,3-diol. Compounds of the formula (XI) containing a trihalomethyl group R' can be obtained, for example, by customary halogenation of a suitable methyl compound, for example with N-chlorosuccinimide or N-bromosuccinimide, or by haloform-analogous degradation of suitable alkanoyl compounds, such as acetyl compounds.

Compounds of the formula (XI) containing an optionally hydrated formyl group R' may furthermore be formed in situ, in the course of the oxidation reaction, for example from the methyl group or aminomethyl group, or from the hydroxymethyl group optionally esterified with an inorganic acid, such as a hydrohalic acid, or with an organic carboxylic acid, such as a lower alkanecarboxylic acid, or may be liberated from one of their derivatives, such as an acetal, acylal or imine, for example from a lower alkyleneacetal or di-lower alkylacetal, a dihalomethyl compound such as a dichloromethyl compound or an optionally substituted benzylimine. Aminodihalomethyl groups or lower alkoxydihalomethyl groups are likewise advantageously prepared in situ by customary partial ammonolysis or iminolysis or alcoholysis of the corresponding trihalomethyl compound.

The compounds of the formula (I) may furthermore be prepared by the process in which, in a compound of the formula (XIII)

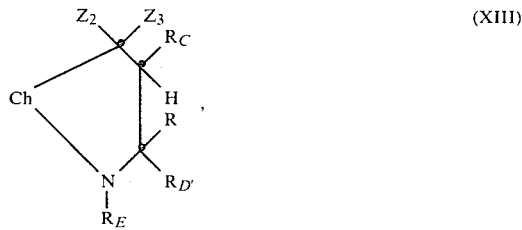

(XIII)

in which
$Z_2$ represents a radical that may be converted into optionally etherified hydroxy, and
$Z_3$ together with $R_C$ and
$R_D$ together with $R_E$ in each case represents an additional link,
or in which
$Z_2$ and $Z_3$ each represents a monovalent radical, or together they represent a divalent radical that may be converted into oxo, and
$R_C$ together with $R_D$ represents an additional link,
or in a salt thereof, a radical $Z_2$, which may be converted into optionally etherified hydroxy, is converted into optionally etherified hydroxy, or radicals $Z_2$ and $Z_3$ or $Z_2+Z_3$, which may be converted into oxo, are converted into oxo, and, if desired, the compound which can thus be obtained is converted into a different compound of the formula (I) and/or a resulting salt-forming compound is converted into a salt, or a resulting salt is converted into the free compound or into a different salt.

Radicals that may be converted into optionally etherified hydroxy are, for example, esterified hydroxy groups, optionally etherified mercapto groups, sulphinyl groups, sulphonyl groups or optionally substituted amino groups. Monovalent radicals that may jointly be converted into the oxo group are, for example, esterified hydroxy groups or hydroxy groups etherified with an open-chain alcohol or mercapto groups etherified with an open-chain mercaptan. Divalent radicals that are represented by $Z_2$ and $Z_3$ together and that may be converted into oxo, are, for example, thioxo, hydroxy groups etherified with a dihydric alcohol, mercapto groups etherified with a divalent mercaptan, or optionally substituted imino groups. Esterified hydroxy groups, are, for example, hydroxy groups esterified with a mineral acid, an organic sulphonic acid or a carboxylic acid, such as a halogen, for example chlorine, bromine or iodine; aliphatic or aromatic sulphonyloxy, for example methanesulphonyloxy, ethanesulphonyloxy, benzenesulphonyloxy or p-toluenesulphonyloxy; or acyloxy derived from an organic carboxylic acid or from a monofunctional carbonic acid derivative, such as a carbonic acid semiester, a haloformic acid or optionally substituted carbamic acid, for example lower alkanoyloxy, optionally substituted benzoyloxy, lower alkoxycarbonyloxy, optionally substituted phenoxycarbonyloxy, chlorocarbonyloxy or bromocarbonyloxy, or optionally substituted carbamoyloxy, such as lower alkylated carbamoyloxy. Etherified mercapto is, for example, mercapto etherified with an aliphatic or aromatic mercaptan, for example lower alkylthio or optionally substituted phenylthio. Substituted amino is, for example, amino mono-substituted by hydroxy or amino, or amino mono-substituted or di-substituted by aliphatic radicals or optionally substituted phenyl, wherein the aliphatic radicals may be monovalent or divalent and the monovalent aliphatic radicals are, for example lower alkyl radicals and divalent aliphatic radicals are, for example lower alkylene radicals, or aza-lower alkylene, oxa-lower alkylene or thia-lower alkylene radicals, for example hydroxyamino, hydrazino, mono- or di-lower alkylamino, optionally substituted anilino, pyrrolidino, piperidino, morpholino, thiamorpholino or N'-lower alkylpiperazino, such as N'-methylpiperazino. Hydroxy etherified with a monohydric alcohol is, for example, lower alkoxy or optionally substituted phenoxy. Hydroxy groups $Z_2+Z_3$ etherified with a dihydric alcohol are, for example, lower alkylenedioxy groups or optionally substituted 1,2-phenylenedioxy groups, for example ethylenedioxy, 1,3-propylenedioxy or 1,2-phenylenedioxy. Mercapto groups etherified with a divalent mercaptan are, for example, lower alkylenedithio groups or optionally substituted 1,2-phenyldithio groups, for example ethylenedithio, 1,3-propylenedithio or 1,2-phenylenedithio. Optionally substituted imino groups are, for example, imino groups substituted by hydroxy, amino, lower alkyl or optionally substituted phenyl, for example oximino, hydrazono, lower alkylimino or anilo.

The conversion of the mentioned groups into optionally etherified hydroxy or into oxo is carried out in the usual manner, preferably by solvolysis, especially by hydrolysis or alcoholysis, that is to say, reaction with water or with the alcohol corresponding to the etherified hydroxy group to be formed. Thus, for example the mentioned groups that may be converted into oxo or hydroxy may be converted into oxo or hydroxy in the usual manner, for example in the presence of an acidic or basic hydrolysing agent, advantageously in a solvent or diluent and if required at elevated or reduced temperature, for example in a temperature range of from 0° to 150° C., under an inert gas, such as nitrogen, and/or in a closed vessel. Acidic hydrolysing agents are, for example, protonic acids, such as mineral acids or the acidic salts thereof, for example hydrochloric, hydrobromic or hydriodic acid, sulphuric acid or alkali metal bisulphates; sulphonic acids, for example p-toluenesulphonic acid or sulphamic acid; organic carboxylic acids, such as lower alkanoic acids; and also acidic ion-exchangers. Basic condensing agents are, for example, alkali metal hydroxides or carbonates, for example sodium or potassium hydroxide or sodium or potassium carbonate and tertiary organic nitrogen gases, for example triethylamine or pyridine. Suitable solvents or diluents are especially water-miscible solvents, such as alcohols, for example lower alkanols; cyclic aliphatic ethers, for example dioxan or tetrahydrofuran; lower aliphatic ketones, for example acetone; tertiary aliphatic amides or lactams, for example dimethylformamide or N-methylpyrrolidone; or aliphatic sulphoxides, for example dimethyl sulphoxide. As already mentioned, reactive esterified hydroxy groups $Z_2$, that is to say, hydroxy groups $Z_2$ esterified with a mineral acid or an organic sulphonic acid, can be converted in accordance with customary alcoholysis methods into etherified hydroxy, for example in the presence of a basic condensing agent, such as an alkali metal hydroxide or alkali metal carbonate, or by using the particular alcohol in the form of an alcoholate, such as an alkali metal alcoholate, preferably in a solvent or diluent, if required whilst heating, for example at temperatures in the range of from approximately 0° to 150° C., under an inert gas, such as nitrogen, and/or in a closed vessel.

The starting substances of the formula XIII can be prepared in accordance with methods known per se.

The compounds of the formula XIII, in which $Z_2$ represents halogen or an optionally substituted amino group, may thus be obtained, for example, by cyclising a compound of the formula XIV

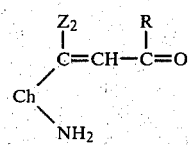
(XIV)

in the usual manner.

From the halogen compounds which may be obtained, for example, in this manner, compounds of the formula XIII, in which $Z_2$ is mercapto can be obtained by reacting with an isothiuronium salt and by subsequent hydrolysis, or by reaction with sodium thioacetate and by subsequent reduction, and compounds of the formula XIII in which $Z_2$ is etherified mercapto can be obtained by reacting with an alkali metal mercaptide. Compounds of the formula XIII in which $Z_2$ is a di-substituted amino group or in which $Z_2$ and $Z_3$ are etherified hydroxy or mercapto, may also be prepared by metallating a compound of the formula XV

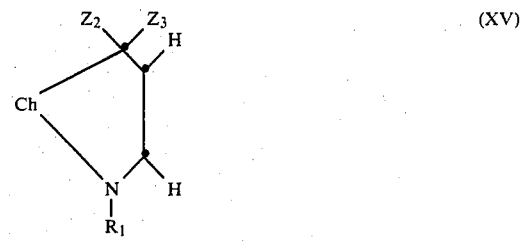

by reacting it with a metallating agent, for example phenylsodium or butyllithium, in the 2-position to the $—N(R_4)—$ group, and subsequently reacting it with a compound of the formula R-Hal (XVI), or with carbon dioxide. Compounds of the formula XIII, in which $Z_2+Z_3$ represents imino, may be obtained, for example, by condensing a corresponding 6-aminoquinoline with a chlorofumaric acid ester nitrile or with acetylenedicarboxylic acid dinitrile, the reaction preferably being carried out in the manner specified for the preparation and intramolecular condensation of compounds of the formula IV and VI.

The compounds of the formula I may furthermore be obtained by oxidising the Ch' radical in a compound of the formula XVI

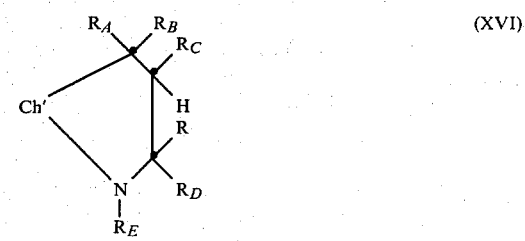

in which Ch' represents a partially hydrogenated radical Ch, or in a salt thereof, to Ch, and, if desired, converting the compound which may be thus obtained into a different compound of the formula I and/or a resulting salt-forming compound into a salt or a resulting salt into the free compound or into a different salt.

The Ch' radical is, for example, a 1,2-dihydro-5,6-quinolinylene radical optionally additionally substituted as specified for the Ch radical.

The oxidation of the Ch' radical to the desired Ch radical can be carried out in a manner known per se, for example by the action of a suitable oxidising agent, if required in the presence of an inert solvent, at elevated temperature, for example at approximately 100° to approximately 300° C., especially at approximately 150° to approximately 250° C., and/or in a closed vessel. Suitable oxidising agents are, for example, aromatic nitro compounds, such as nitrobenzene, 2,4-dinitrochlorobenzene or picric acid; inorganic oxidising agents, such as oxyacids of hexavalent sulphur or of pentavalent phosphorus or arsenic or the anhydrides thereof, such as sulphuric acid, phosphorus pentoxide or arsenic pentoxide; metal oxides, such as iron(III) oxide; or organic carbonyl compounds, such as quinones, and especially α,β-unsaturated aliphatic aldehydes and ketones.

The starting substances of the formula (XVI) are advantageously prepared in situ, for example by reacting a corresponding 6-aminoquinoline, for example of the formula

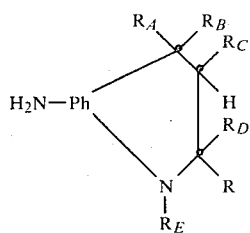

(XVII)

in which Ph is a 1,2-phenylene radical carrying the amino group in p-position with respect to the —N(-$R_E$)— group, or an acid addition salt, with a corresponding $\alpha,\beta$-unsaturated aliphatic aldehyde or ketone, for example with acrolein, in the presence of an acidic condensing agent, such as a Lewis acid, for example aluminium trichloride or zinc chloride, or a mineral acid, such as hydrochloric acid, sulphuric acid or phosphoric acid, or an anhydride of one of these, for example phosphorus pentoxide. The $\alpha,\beta$-unsaturated aldehydes or ketones to be used as starting substances are advantageously likewise produced in situ, for example by autocondensation of a saturated aliphatic aldehyde, such as acetaldehyde, or ketone, such as acetone, or, for the in situ formation of acrolein, by dehydration of glycerin or the esters thereof.

Compounds of the formula I, in which $R_A + R_B$ represents oxo, $R_C + R_D$ represents an additional link and $R_E$ represents hydrogen, may furthermore be prepared by splitting off $Z_4$ from a compound of the formula XVIII

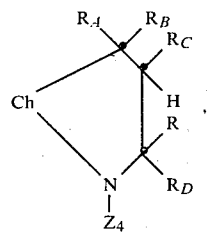

(XVIII)

in which $Z_4$ is a radical capable of being split off, or from a salt thereof and, if desired, converting the compound which may be thus obtained into a different compound of the formula I and/or converting a resulting salt-forming compound into a salt or a resulting salt into the free compound or into a different salt.

Radicals capable of being split off are, for example, acyl radicals, such as acyl groups derived from carboxylic acids, for example organic carboxylic acids or monofunctional derivatives of carbonic acid, or $\alpha$-phenyl-lower alkyl groups optionally substituted in the phenyl moiety. Acyl radicals of organic carboxylic acids are, for example, optionally halogenated lower alkanoyl radicals, such as acetyl, propionyl, butyryl and trifluoroacetyl, or optionally substituted benzoyl radicals, such as benzoyl, 3,5-dichlorobenzoyl, 4-nitrobenzoyl and 2,4-dinitrobenzoyl. Acyl groups derived from monofunctional carbonic acid derivatives are, for example, esterified carboxy groups, halocarbonyl groups or optionally substituted carbamoyl groups. Esterified carboxyl groups are, for example, optionally halogenated lower alkoxycarbonyl groups, such as lower alkoxycarbonyl, for example methoxycarbonyl, ethoxycarbonyl or tert.-butoxycarbonyl, mono-, di- or trihalo-lower alkoxycarbonyl groups, for example 2-iodoethoxycarbonyl, 2,2,2-tribromoethoxycarbonyl or 2,2,2-trichloroethoxycarbonyl; optionally substituted $\alpha$-phenyl-lower alkoxycarbonyl radicals, for example benzyloxycarbonyl; optionally substituted phenoxycarbonyl; 2-sulphonyl-lower alkoxycarbonyl radicals, for example 2-(4-toluenesulphonyl)ethoxycarbonyl; or etherified 2-mercapto-lower alkoxycarbonyl radicals, for example 2-(4-tolylthio)ethoxycarbonyl. Substituted carbamoyl is, for example, carbamoyl substituted by lower alkyl or lower alkylene, or by aza-, oxa- or thia-lower alkylene, for example N,N-dimethylcarbamoyl, pyrrolidinocarbonyl, piperidinocarbonyl, morpholinocarbonyl, thiamorpholinocarbonyl, or N'-lower alkyl piperazinocarbonyl. $\alpha$-Phenyl-lower alkyl radicals optionally substituted in the phenyl moiety are especially corresponding benzyl radicals.

The splitting off of the mentioned radicals is carried out, for example, by solvolysis, especially by hydrolysis, if required in the presence of an acidic or basic hydrolysing agent, in a suitable solvent or diluent, whilst cooling or heating, for example within the temperature range of from approximately 0° to 150° C., under an inert gas, such as nitrogen, and/or in a closed vessel. Acidic hydrolysing agents are, for example protonic acids, such as mineral acids, for example hydrochloric, hydrobromic and hydriodic acid, sulphuric acid or phosphoric acid; sulphonic acids for example methanesulphonic acid, ethanesulphonic acid, benzenesulphonic acid or p-toluenesulphonic acid; sulphamic acid; or organic carboxylic acids, such as lower alkanoic acids, for example acetic or formic acid. Basic hydrolysing agents are, for example, alkali metal hydroxides or carbonates, for example sodium hydroxide or carbonate or potassium hydroxide or carbonate, ammonia and amines. Suitable solvents are especially water-miscible solvents. The solvolytic splitting off, for example, of acyl, may furthermore be carried out by ammonolysis or aminolysis, for example by reacting ammonia or an amine, such as hydrazine or a mono- or di-lower alkylamine or alkyleneamine or azaalkyleneamine, oxa-alkyleneamine or thia-alkyleneamine, for example with ammonia, hydrazine, methylamine, dimethylamine, morpholine or piperidine, if required in an inert solvent, whilst cooling or heating, for example in a temperature range of from approximately −20° to 100° C., and/or in a closed vessel.

Optionally substituted $\alpha$-phenyl-lower alkoxycarbonyl groups and suitably halogenated lower alkoxycarbonyl radicals may also be split off by reduction. These groups are split off in the usual manner, especially by methods known from the literature for analogous splitting off reactions. Starting from optionally substituted $\alpha$-phenyl-lower alkoxycarbonyl radicals, hydrogen is, for example, allowed to act on the compound to be reduced in the presence of a hydrogenating catalyst, such as a palladium, platinum or nickel catalyst, for example optionally sulphidised palladium on carbon, platinum, optionally on potassium carbonate, or Raney nickel, if required in a suitable solvent, at normal or elevated pressure, for example at approximately 0.5 to 20 bar and/or whilst cooling or heating, for example in a temperature range of from approximately 0° to 80° C., advantageously in a closed vessel. 2-halo-lower alkoxycarbonyl radicals, such as 2,2,2-trichloroethoxycarbonyl or 2-iodoethoxycarbonyl, can be reduced especially by metallic reduction, for example by treating with non-noble metals or metal alloys, such as amalgams, especially zinc, or activated aluminium, such as aluminium treated with a solution of a mercury salt, usually in the presence of a protonic acid, such as an organic carboxylic acid, for example acetic acid, if required whilst cooling or heating, for example at −30° to 100° C. 2-halo-lower alkoxycarbonyl radicals may furthermore be reduced by the action of chromium(II) compounds, for example chromium(II) chloride or chromium(II) acetate.

The starting substances of the formula XVIII may be prepared in accordance with methods known per se, for example by cyclisation of a compound of the formula H—C—(NZ$_4$)—CR=CH—COOH (XIX), or of a suitable functional derivative thereof, such as an ester or anhydride, especially in a manner analogous to the method described for the intramolecular condensation of compounds of the formula IV.

A compound of the formula I obtainable according to the invention may be converted in a manner known per se into a different compound of the formula I.

Thus, in a compound of the formula I, carboxy R may be converted into an esterified carboxy group in accordance with esterification processes known per se. The esterification may thus, for example, be carried out by treatment with an alcohol in the presence of a suitable condensing agent, such as a dehydrating agent, for example dicyclohexyl carbodiimide, or a mineral acid, for example sulphuric acid or hydrochloric acid, or, to form a hydroxy-lower alkyl group, reaction with a corresponding epoxy-lower alkane may be carried out. The esterification may furthermore be carried out by treating with a suitable N,N-di-lower alkylformamide acetal, for example N,N-dimethylformamide diethylacetal, with N,N,O-trimethylformamidinium methosulphate, with a carbonate or pyrocarbonate, for example with diethyl(pyro)carbonate, or with an organic sulphite or phosphite, such as a di-lower alkylsulphite or tri-lower alkylphosphite, the latter in the presence of a suitable acidic medium, for example p-toluenesulphonic acid. An acid of the formula I to be esterified, in which the free carboxy group is present in salt form, for example in the form of an alkali metal salt such as the sodium salt, may, furthermore, be reacted with a reactive ester of an alcohol, for example a strong acid, such as a corresponding halide, for example a chloride, bromide or iodide, or with sulphuric acid ester. The esterification may, however, alternatively be carried out by reaction with a lower alkene corresponding to the lower alkoxy group to be introduced, preferably in the presence of an acidic condensing agent, such as a strong protonic acid, for example sulphuric acid, or a Lewis acid, for example boron trifluoride etherate. Substituents optionally present in one of the esterification reagents mentioned may be in a functionally modified form, and may then be liberated in a compound of the formula I in which R represents substituted lower alkoxycarbonyl in which substituents are present in functionally modified form. It is thus possible, for example, to use 2,3-epoxypropyl chloride as esterifying reagent and subsequently to hydrolyse the 2,3-epoxypropoxy grouping in the resulting ester to the desired 2,3-dihydroxypropoxy grouping.

In compounds of the formula I, esterified carboxy R may moreover be converted into a different esterified carboxy group, for example by transesterification, for example by treating with an alcohol, if required in the presence of a suitable transesterifying catalyst, such as a relevant alkali metal alcoholate, for example the relevant sodium or potassium alcoholate, or in the presence of a mineral acid, for example sulphuric acid, or hydrochloric acid.

In compounds of the formula I, free or esterified carboxy R may furthermore be converted in a manner known per se into optionally substituted carbamoyl. An ester of the formula I may thus, for example, be treated with ammonia, hydroxylamine or a corresponding primary or secondary amine and in this manner be converted into amides of the formula I. Furthermore, the ammonium salt or an amine salt of an acid of the formula I may be converted into an amide of the formula I by dehydration, for example, whilst heating or by the action of a suitable hydrating agent, such as sulphuric acid or N,N-dicyclohexyl carbodiimide.

The conversion of carboxy R into esterified or amidated carboxy may, however, alternatively be carried out by reactive modification of the carboxy group, for example anhydridisation by reaction with an acid anhydride, for example thionyl chloride, phosphorus pentachloride or a lower alkanoic acid anhydride, such as acetic anhydride, and conversion into a reactive ester, for example by reaction with 4-nitrophenol, or into a reactive amide, for example by reaction with N,N′-bis(1-imidazoyl)urea, and subsequent reaction with the relevant alcohol, or with ammonia or the relevant amine having at least one hydrogen atom.

In compounds of the formula I, an esterified or amidated carboxy group R may be converted into the free carboxy group in the usual manner, for example by hydrolysis, usually in the presence of an acidic or basic hydrolysing agent such as a mineral or carboxylic acid, for example hydrochloric acid, sulphuric acid or acetic acid, or in the presence of an alkali metal hydroxide or carbonate, for example sodium hydroxide or carbonate or potassium hydroxide or carbonate.

Furthermore, in compounds of the formula I, in which $R_A$ and $R_B$ together represent oxo, $R_C$ and $R_D$ together represent an additional link and $R_E$ represents hydrogen, or in which $R_A$ is hydroxy, and $R_B$ together with $R_C$ and $R_D$ together with $R_E$ in each case represents an additional link, substitution can be effected in the usual manner at the nitrogen atom by a radical $R_1$ other than hydrogen, or etherification can be carried out at the oxygen atom in the 4-position. The substitution of the ring nitrogen atom by $R_1$, and the etherification of a ring-bonded hydroxy group $R_A$, is carried out in the usual manner, for example by reaction with a reactive ester of a suitable alcohol, if required in the presence of a basic condensing agent, such as an alkali metal hydride, amide, alcoholate or hydroxide, for example sodium hydride, sodium amide, lithium diisopropylamide, sodium methylate, potassium tert.-butylate or potassium hydroxide, whilst cooling or heating, for example in a temperature range of from approximately 0° to 120° C., under an inert gas, such as nitrogen, and/or in a closed vessel. Reactive esters of suitable alcohols are especially mineral acid esters, such as hydrohalic acid esters or sulphuric acid esters, or organic sulphonic acid esters, for example methanesulphonic, ethanesulphonic, benzenesulphonic, p-toluenesulphonic of fluorosulphonic acid esters. In the treatment of an ester of the formula I with an alkyl halide in the presence of sodium hydride in dimethylformamide derivatives, alkylated in most cases at the 4-positioned oxygen atom, are obtained.

Furthermore, in compounds of the formula I additional substituents, preferably lower alkyl groups and/or halogen, may be introduced into the Ch radical.

Thus, for example lower alkyl may be introduced by reacting with a lower alkyl halide, a lower alkanol or a lower alkene in the presence of a Lewis acid, for example aluminium trichloride, or halogen may be introduced in the usual manner, for example by reacting with the halogen in the presence of a Lewis acid, such as the corresponding iron halide, which may also be formed in situ from finely divided iron and the halogen, or by treating with N-chlorosuccinimide.

Furthermore, hydroxy as a substituent of Ch may be converted into lower alkoxy in the usual manner, for example by reacting with a reactive ester of a lower alkanol, such as a lower alkyl halide or di-lower alkyl sulphate, advantageously in the presence of a basic condensing agent, such as an alkali metal hydroxide or carbonate, for example potassium carbonate in amyl alcohol or acetone.

Salt-forming compounds of the formula I may be converted into salts in a manner known per se, for example by treating with a base or an acid, usually in the presence of a solvent or diluent. Resulting salts may be converted into the free compounds in a manner known per se, for example by treating with an acidic reagent, such as a mineral acid, or with a basic reagent, such as an alkali metal hydroxide. The compounds of the formula I, including the salts thereof, may also be obtained in the form of their hydrates, or may include the solvent used for crystallisation. Owing to the close relationship between the compounds of the formula I in free form and in the form of their salts, hereinbefore and hereinafter free compounds shall also include the salts thereof, and the salts shall also include the free compounds.

The invention relates also to those forms of the process in which a product obtainable as intermediate at any stage of the process is used as starting substance and the remaining process steps are carried out, or a starting substance is formed under the reaction conditions or used in the form of a derivative or optionally in the form of a salt. In the process of the present invention, the starting substances are preferably those which result in the compounds initially described as being especially valuable. The present invention also relates to new starting substances, analogous processes for their preparation and their use.

The compounds of the formula I and their salts exhibit valuable pharmacological properties. In particular, they have an anti-allergic action, which may be demonstrated, for example, in rats, at doses from approximately 1 mg/kg when administered intravenously and in doses from approximately 10 mg/kg when administered orally in a passive cutaneous anaphylaxis test (PCA reaction), which is carried out analogously to the method described by Goose and Blair, Immunology, Vol. 16, p. 794 (1969). The passive cutaneous anaphylaxis is produced in accordance with the process described by Ovary, Progr. Allergy, Vol. 5, p. 459 (1958). The anti-allergic, and especially the degranulation-inhibiting, action of the compounds of formula I and the salts thereof can also be observed in vitro by way of the release of histamine from peritoneal cells of the rat in the dosage range of from approximately 0.1 to approximately 100 mg/l in the case of immunologically-induced release, for which, for example, rats infected with *Nippostrongilus brasiliensis,* are used, and in the dosage range of from approximately 1.0 to approximately 100 mg/l in the case of chemically-induced release brought about for example by a polymer of N-4-methoxyphenylethyl-N-methylamine. The compounds of the present invention are consequently useful as inhibitors of allergic reactions, for example in the treatment and prophylaxis of allergic disorders, such as bronchial asthma, both of the extrinsic and of the intrinsic form, or as inhibitors of other allergic disorders, such as allergic rhinitis, for example hay fever, conjunctivitis, or allergic dermatites, for example urticaria or eczemas.

As already mentioned, the present invention also relates to pharmaceutical preparations that contain compounds of the formula I or pharmaceutically suitable salts of the same. The pharmaceutical preparations according to the invention are for enteral administration, such as oral, nasal or rectal administration, or for parenteral or buccal administration to mammals, and the preparations contain the pharmacological active substance alone or together with a pharmaceutically acceptable carrier. The dosage of the active substance depends on the species of mammal, the age and the individual condition and on the method of administration.

The pharmaceutical preparations according to the invention contain, for example, up to approximately 95%, preferably from approximately 5% to approximately 90%, of the active substance. Pharmaceutical preparations according to the invention are, for example, in unit dosage form, such as dragées, tablets, capsules, suppositories or ampoules, or in the form of inhalation preparations and pharmaceutical formulations for topical or local use, for example for insufflation.

The pharmaceutical preparations of the present invention are prepared in a manner known per se, for example by means of conventional mixing, granulating, dissolving or lyophilising processes. Pharmaceutical preparations for oral application may, for example, be obtained by combining the active substance with solid carriers, optionally granulating the resulting mixture and processing the mixture or granulate, if desired or necessary after the addition of suitable auxiliaries, to form tablets or dragée cores. Suitable carriers are especially fillers, such as sugars, for example lactose, saccharose, mannitol or sorbitol, cellulose preparations and/or calcium phosphates, for example tri-calcium phosphate or calcium biphosphate; also binders, such as starch pastes, for example, corn, wheat, rice or potato starch pastes, gelatin, tragacanth, methylcellulose and/or polyvinylpyrrolidone; and/or, if desired, disintegrating agents, such as the above-mentioned starches; carboxymethyl starches, transversely cross-linked polyvinylpyrrolidone, agar, alginic acid or a salt thereof, such as sodium alginate. Auxiliaries are especially flow regulators and lubricants, for example silica, talc, stearic acid or salts thereof, such as magnesium or calcium stearate, and/or polyethylene glycol. Dragée cores are provided with suitable coatings that are optionally resistant to gastric juice, for which there are used, for example, concentrated sugar solutions that optionally contain gum arabic, talc, polyvinylpyrrolidone, polyethylene glycol and/or titanium dioxide, a coating solution in suitable organic solvents or solvent mixtures, or, for the preparation of coatings resistant to gastric juice, a solution of suitable cellulose preparations, such as acetyl cellulose phthalate or hydroxypropylmethylcellulose phthalate. Dyes or pigments may be added to the tablets or dragée coatings, for example to identify or characterise different doses of active substance. Other pharmaceutical preparations that may be administered orally are push-fit capsules made of gelatin, and also soft, sealed capsules consisting of gelatin and a plasticiser, such as glycerin or sorbitol. The push-fit capsules may contain the active substance in the form of a granulate, for example in admixture with fillers, such as lactose, binders, such as starches, and/or lubricants, such as talc or magnesium stearate, and optionally stabilisers. In soft capsules, the active substance is preferably dissolved or suspended in suitable liquids, such as fatty oils, paraffin oil or liquid polyethylene glycols, and stabilisers may likewise be added.

Pharmaceutical preparations for rectal administration are, for example, in the form of suppositories consisting of a combination of the active substance and a suppository base composition. Suitable base compositions for suppositories are, for example, natural or synthetic triglycerides, paraffin hydrocarbons, polyethylene glycols and higher alkanols. It is also possible to use gelatin rectal capsules that contain a combination of the active substance and a base composition. Suitable base compositions are liquid triglycerides, polyethylene glycols and paraffin hydrocarbons.

For parenteral administration aqueous solutions of the active substance in water-soluble form, for example in the form of a water-soluble salt, are especially suitable; also suitable are suspensions of the active substance, such as corresponding oily injection suspensions, for which suitable lipophilic solvents or vehicles, such as fatty oils, for example sesame oil or synthetic fatty acid esters, for example ethyl oleate or triglycerides are used; or aqueous injection suspensions that contain substances increasing viscosity, for example sodium carboxymethylcellulose, sorbitol and/or dextran and, optionally, stabilisers.

Inhalants for the treatment of the respiratory passages by nasal or buccal administration are, for example, in the form of aerosols or sprays, which are able to distribute the pharmacological active substance in the form of a powder or in the form of drops of a solution or suspension. Preparations with powder-distributing properties usually contain, in addition to the active substance, a liquid propellant gas having a boiling point below room temperature and, if desired, carriers, such as liquid or solid, non-ionic or anionic, surfactants and/or solid diluents. Preparations in which the pharmacological active substance is present in solution contain, in addition thereto, a suitable propellant, and also if necessary, an additional solvent and/or a stabiliser. Instead of the propellant gas, compressed air may be used, and this can be produced by means of a suitable compression and decompression device as required.

Pharmaceutical preparations for topical and local use are, for example for treatment of the skin, in the form of lotions or creams that contain a liquid or semi-solid oil-in-water or water-in-oil emulsion, and salves, optionally containing a preservative; for treatment of the eyes, in the form of eye drops that contain the active compound in aqueous or oily solution and eye salves, which are preferably manufactured in sterile form; for the treatment of the nose, in the form of powders, aerosols and sprays, (similarly to those described above for the treatment of the respiratory passages), and also coarse powders, which are administered by rapid inhalation through the nose, and nose drops that contain the active compound in aqueous or oily solution; or for the local treatment of the mouth, lozenges that contain the active compound in a composition generally consisting of sugar and gum arabic or tragacanth, to which taste correctives may be added, and also pastilles that contain the active substance in an inert composition consisting, for example, of gelatin and glycerin or sugar and gum arabic.

Finally, the invention relates to the use of compounds of the formula I or the salts thereof as pharmacologically active compounds, especially as anti-allergic agents, preferably in the form of pharmaceutical preparations. The daily dose administered to a mammal of about 70 kg body weight is, depending on the form of application, from approximately 100 mg to approximately 1000 mg, preferably from approximately 250 mg to approximately 750 mg.

The following examples illustrate the above-described invention: they are not, however, intended to restrict its scope in any way. Temperatures are given in degrees Centigrade.

EXAMPLE 1

A solution of 24 g of 1-[N-(8-methoxyquinolin-6-yl)]-2-aminofumaric acid dimethyl ester in 300 ml of diphenyl ether is refluxed for 10 minutes. The solution is allowed to cool to room temperature, 200 ml of diethyl ether are added, and filtration and recrystallisation from dimethylformamide are carried out. 6-Methoxy-1-oxo-1,4-dihydro-4,7-phenanthroline-3-carboxylic acid methyl ester having a melting point of 280° (decomposition) is obtained.

The starting material may be obtained, for example, as follows:

24 g of acetylenedicarboxylic acid dimethyl ester are added to a solution of 26 g of 6-amino-8-methoxy-quinoline in 300 ml of methanol, the solution is allowed to stand for one hour at room temperature and evaporated to dryness under reduced pressure. The residue is recrystallised from ethanol. 1-[N-(8-methoxyquinolin-6-yl)]-2-aminofumaric acid dimethyl ester having a melting point of 155° is obtained.

EXAMPLE 2

5 g of 6-methoxy-1-oxo-1,4-dihydro-4,7-phenanthroline-3-carboxylic acid methyl ester are dissolved in 100 ml of N-sodium hydroxide solution and refluxed for one hour. The solution is allowed to cool to room temperature and is acidifed with dilute hydrochloric acid to a pH of 5. After standing for a short while, 6-methoxy-1-oxo-1,4-dihydro-4,7-phenanthroline-3-carboxylic acid having a melting point of 286°–228° (decomposition) crystallises out.

EXAMPLE 3

In a manner analogous to that described in Examples 1 and 2, the following may also be prepared. 6-methoxy-1-oxo-1,4-dihydro-4,7-phenanthroline-3-carboxylic acid ethyl ester, melting point 225°, 6-methoxy-1-oxo-1,4-dihydro-4,7-phenanthroline-3-carboxylic acid propyl ester, melting point 202°–204°, 6-methoxy-1-oxo-1,4-dihydro-4,7-phenanthroline-3-carboxylic acid n-butyl ester, melting point 212°–213°, 1-ethoxy-6-methoxy-4,7-phenanthroline-3-carboxylic acid methyl ester, melting point 188°–190°, and 6-n-butoxy-1-oxo-1,4-dihydro-4,7-phenanthroline-3-carboxylic acid methyl ester.

EXAMPLE 4

30 mg of sodium hydride are added whilst stirring to 150 ml of absolute n-butanol. The reaction vessel is provided with a Soxhlet extraction attachment, and this is charged with 6 g of 6-methoxy-1-oxo-1,4-dihydro-4,7-phenanthroline carboxylic acid methyl ester. At a bath temperature of 160° to 180°, the solution is extracted for 13 hours under nitrogen, and the extraction solution is subsequently evaporated to dryness under reduced pressure. A little ice-water is added to the residue and the whole is extracted three times with 100 ml of chloroform each time. The extracts are combined, dried over sodium sulphate and evaporated to dryness under reduced pressure. 6-methoxy-1-oxo-1,4-dihydro-4,7-phenanthroline-3-carboxylic acid butyl ester is obtained, which melts at 212°–213° after recrystallisation from a mixture of ethanol, petroleum ether and diethyl ether.

EXAMPLE 5

In an analogous manner to that described in Example 4, by reacting 4 g of 6-methoxy-1-oxo-1,4-dihydro-4,7-phenanthroline-3-carboxylic acid methyl ester with propanol, 6-methoxy-1-oxo-1,4-dihydro-4,7-phenanthroline-3-carboxylic acid propyl ester having a melting point of 202°–204° is obtained (from toluene).

EXAMPLE 6

1.2 g of sodium hydride (50% suspension in mineral oil) is added to a solution of 6.5 g of 6-methoxy-1-oxo-1,4-dihydro-4,7-phenanthroline-3-carboxylic acid methyl ester in 50 ml of absolute dimethylformamide, whilst stirring at 40° in an inert gas atmosphere. After 30 minutes the reaction mixture is allowed to cool to room temperature, 4.3 g of ethyl iodide are added in portions, the mixture is stirred for 6 hours, 200 ml of ice-water are added, the mixture is extracted by shaking with 50 ml of petroleum ether and then extracted three times with 200 ml of chloroform each time. The chloroform extracts are combined, washed with water, dried over sodium sulphate and concentrated by evaporation under reduced pressure. 1-ethoxy-6-methoxy-4,7-phenanthroline-3-carboxylic acid methyl ester is obtained which, after recrystallisation from ethanol, melts at 188°–190°.

EXAMPLE 7

2 g of anhydrous potassium tert.-butylate are added to a solution of 2.5 g of N-(5-acetyl-8-methoxyquinolin-6-yl)oxamide acid methyl ester in 50 ml of anhydrous N,N-dimethylformamide and the whole is heated, with the exclusion of water, for 10 hours at 130°. The solution is then allowed to cool and is evaporated to dryness in vacuo. The residue is treated in succession with 2 N acetic acid and water. By chromatographic purification on silica gel and fractionated crystallisation from N,N-dimethylformamide, the 6-methoxyy-1-oxo-1,4-dihydro-4,7-phenanthroline-3-carboxylic acid methyl ester having a melting point of 280° (with decomposition) is obtained.

The starting material can be obtained, for example, as follows:

2.6 g of chloroglyoxylic acid methyl ester are added until dripping wet to a solution of 4.3 g of 5-acetyl-6-amino-8-methoxyquinoline in 100 ml of anhydrous pyridine whilst stirring at 10°. After the addition is complete, the solution is stirred for 3 hours at room temperature and evaporated to dryness at 40° in vacuo. 50 ml of saturated sodium bicarbonate solution are added to the residue and extraction is carried out several times with ethyl acetate and chloroform. The organic extracts are dried over sodium sulphate, and concentrated by evaporation in vacuo. The crude N-(5-acetyl-8-methoxyquinoline-6-yl)oxamide methyl ester obtained in this manner is immediately further processed.

EXAMPLE 8

2 g of palladium (5% on active carbon) is added to a solution of 5.3 g of crude 4-(6-nitro-8-methoxyquinolin-5-yl)-2,4-dioxobutyric acid ethyl ester in 200 ml of acetic acid, and the solution is then hydrogenated until 3 equivalents of hydrogen have been absorbed. The solution is then filtered off the catalyst whilst hot, 2 ml of concentrated hydrochloric acid are added thereto and the solution is then evaporated to dryness. The residue is treated in succession with saturated aqueous sodium bicarbonate solution and water. After the chromatographic purification on silica gel, by fractionated crystallisation from dimethylformamide/ethanol 6-methoxy-1-oxo-1,4-dihydro-4,7-phenanthroline-3-carboxylic acid ethyl ester having a melting point of 255° is obtained. The starting material may be prepared, for example, as follows:

30 ml of oxalic acid diethyl ester are added to a solution of 10 g of 5-acetyl-6-nitro-8-methoxyquinoline in 200 ml of ethanol and 3 g of sodium ethylate, and refluxed, whilst stirring, for 12 hours with the exclusion of water. 100 ml of toluene are then added and the reaction mixture is heated for a further 5 hours, then evaporated to dryness in vacuo and the residue triturated first with 2 N acetic acid then with water. The crude 4-(6-nitro-8-methoxyquinolin-6-yl)-2,4-dioxobutyric acid ethyl ester obtained in this manner is further processed without further purification.

EXAMPLE 9

2 g of sodium ethylate are added to a solution of 6.2 g of 1-chloro-6-methoxy-4,7-phenanthroline-3-carboxylic acid methyl ester in 100 ml of anhydrous N,N-dimethylformamide and the mixture is heated, whilst stirring and with the exclusion of water, for 10 hours at 100°. The solution is then evaporated to dryness in vacuo, the residue is divided between three times 200 ml of chloroform and 200 ml of water, the organic phases are dried over sodium sulphate and evaporated to dryness in vacuo. By fractionated crystallisation from ethanol, the 1-ethoxy-6-methoxy-4,7-phenanthroline-3-carboxylic acid methyl ester having a melting point of 188°–190° is obtained from the residue.

The starting material may be prepared as follows:

100 ml of phosphorus oxychloride are added to 10 g of 1-[N-(8-methoxyquinolin-6-yl)]-2-aminofumaric acid dimethyl ester and the solution is heated to boiling for 15 minutes whilst stirring and with the exclusion of water. The solution is then evaporated to dryness in vacuo, the residue is divided between three times 200 ml of chloroform and 200 ml of saturated aqueous sodium bicarbonate solution. The organic phases are dried over sodium sulphate and concentrated by evaporation in vacuo. The 1-chloro-6-methoxy-4,7-phenanthroline-3-carboxylic acid methyl ester obtained in this manner is further processed without further purification.

EXAMPLE 10

8.4 g of 1-amino-6-methoxy-1,4-dihydro-4,7-phenanthroline-3-carboxylic acid nitrile are refluxed in 200 ml of ethanolic hydrochloric acid (6 N) over night. The solution is then evaporated to dryness under reduced pressure, washed twice with water, and boiled out three times with 250 ml of 2 N sodium hydroxide solution each time. The extracts are combined, weakly acidified with concentrated hydrochloric acid and left to crystallise. The 6-methoxy-1-oxo-1,4-dihydro-4,7-phenanthroline-3-carboxylic acid having a melting point of 286°–288° is obtained.

The starting material may be obtained, for example, as follows:

16.2 g of 6-amino-8-methoxyquinoline are dissolved in 300 ml of ethanol, 8 g of acetylenedicarboxylic acid dinitrile are added and the solution is stirred for 2 hours at room temperature. The solution is then evaporated to dryness under reduced pressure and recrystallised from ethanol. The 1-imino-6-methoxy-1,4-dihydro-4,7-phenanthroline-3-carboxylic acid nitrile is obtained which can be used further without further purification.

EXAMPLE 11

A 1% aqueous solution of 6-methoxy-1-oxo-1,4-dihydro-4,7-phenanthroline-3-carboxylic acid suitable for inhalation may be prepared as follows:

Composition (for 100 ml)

6-methoxy-1-oxo-1,4-dihydro-4,7-phenanthroline-3-carboxylic acid.
Sodium-4-ethoxy-6-butyryl-7-methylquinoline methyl ester: 1.000 g
Di-sodium salt of ethylenediaminetetraacetic acid (stabiliser): 0.010 g
Benzalkonium chloride (preservative): 0.010 g
Water, distilled: ad 100 ml 6-Methoxy-1-oxo-1,4-dihydro-4,7-phenanthroline-3-carboxylic acid is dissolved, with the addition of the equivalent amount of sodium hydroxide, in freshly distilled water, and the disodium salt of ethylenediaminetetraacetic acid and benzalkonium chloride, which is a mixture of alkyldimethylbenzylammonium chlorides in which alkyl contains from 8 to 18 carbon atoms, are added to the solution. After the components have dissolved completely, the resulting solution is made up to a volume of 100 ml with water, introduced into a container and closed in a gas-tight manner.

EXAMPLE 12

Capsules suitable for insufflation containing 0.025 g of 6-methoxy-1-oxo-1,4-dihydro-4,7-phenanthroline-3-carboxylic acid methyl ester may be prepared as follows:

Composition (for 1000 capsules)

6-methoxy-1-oxo-1,4-dihydro-4,7-phenanthroline-3-carboxylic acid methyl ester: 25.00 g
lactose, ground: 25.00 g.

The 6-methoxy-1-oxo-1,4-dihydro-4,7-phenanthroline-3-carboxylic acid methyl ester and the lactose (extremely finely ground) are thoroughly mixed together. The resulting powder is sieved and introduced in portions of 0.05 g into each gelatin capsule.

EXAMPLE 13

Tablets containing 100 mg of 6-methoxy-1-oxo-1,4-dihydro-4,7-phenanthroline-3-carboxylic acid methyl ester as the active substance may be prepared, for example, in the following composition:

| Composition | per tablet |
| --- | --- |
| Active substance | 100 mg |
| lactose | 50 mg |
| corn starch | 73 mg |

| -continued | |
| --- | --- |
| Composition | per tablet |
| colloidal silica | 13 mg |
| talc | 12 mg |
| magnesium stearate | 2 mg |
| | 250 mg |

Preparation

The active substance is mixed with the lactose, a portion of the corn starch and with colloidal silica and the mixture is pressed through a sieve. A further portion of corn starch is mixed on a water bath to a paste with 5 times the amount of water, and the powder mixture is kneaded with this paste until a slightly plastic composition is formed. This composition is pressed through a sieve having a mesh width of approximately 1 mm, dried, and the dried granulate is again pressed through a sieve. The remaining corn starch, the talc and the magnesium stearate are then admixed. The resulting tabletting mixture is compressed to form 250 mg tablets having a break groove or grooves.

EXAMPLE 14

In a manner analogous to that described in Examples 11 to 13, it is also possible to prepare pharmaceutical preparations containing
6-methoxy-1-oxo1,4-dihydro-4,7-phenanthroline-3-carboxylic acid,
6-methoxy-1-oxo-1,4-dihydro-4,7-phenanthroline-3-carboxylic acid ethyl ester,
6-methoxy-1-oxo-1,4-dihydro-4,7-phenanthroline-3-carboxylic acid propyl ester,
6-methoxy-1-oxo-1,4-dihydro-4,7-phenanthroline-3-carboxylic acid n-butyl ester,
1-ethoxy-6-methoxy-4,7-phenanthroline-3-carboxylic acid methyl ester and
6-n-butoxy-1-oxo-1,4-dihydro,4,7-phenanthroline-3-carboxylic acid acid methyl ester,
optionally in the form of acid addition salts, especially the hydrochlorides, carboxylic acids, and in the form of the sodium salts.

EXAMPLE 15

In a manner analogous to that described in Examples 1 to 10, also
6-butoxy-1-oxo-1,4-dihydro-4,7-phenanthroline-3-carboxylic acid butyl ester and
1-ethyl-6-methoxy-1-oxo-1,4-dihydro-4,7-phenanthroline-3-carboxylic acid butyl ester can be prepared.

We claim:

1. A 4,7-phenanthroline derivative of the formula

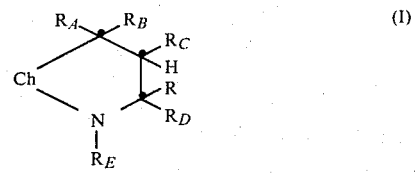

in which
Ch represents 5,6-quinolinylene which is unsubstituted or c-substituted by one or two substituents selected from the group consisting of lower alkyl, lower alkoxy, hydroxy and/or halogen, R represents carboxy, lower alkoxycarbonyl, hydroxylower alkoxycarbonyl, lower alkoxy-lower alkoxycarbonyl, di-lower alkylamino-lower alkoxycarbonyl, and in which either $R_A$ and $R_B$ together represent oxo, $R_C$ and $R_D$ together represent an additional link and $R_E$ represents hydrogen, or $R_A$ represents hydroxy, lower alkoxy or lower alkenyloxy and $R_B$ together with $R_C$ and $R_D$ together with $R_E$ in each case represents an additional link, or a pharmaceutically acceptable salt of a salt-forming compound of the formula (I).

2. A compound according to claim 1, of the formula (Ia)

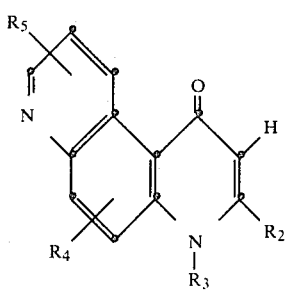

in which $R_2$ represents carboxy, lower alkoxycarbonyl having up to 5 carbon atoms, hydroxy-lower alkoxycarbonyl having up to 5 carbon atoms, lower alkoxy-lower alkoxycarbonyl having up to 4 carbon atoms in each of the alkoxy moieties, di-lower alkylaminolower alkoxycarbonyl having up to 4 carbon atoms in each of the alkyl and alkoxy moieties, $R_3$ represents hydrogen, and $R_4$ and $R_5$ independently of one another, each represents hydrogen, lower alkyl having up to 4 carbon atoms, lower alkoxy having up to 4 carbon atoms, hydroxy, or halogen of an atomic number up to and including 35, or a pharmaceutically acceptable salt of a salt-forming compound of the formula (Ia).

3. A compound according to claim 1 of the formula (Ib)

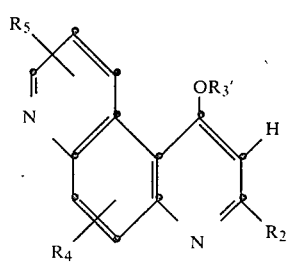

in which $R_2$ represents carboxy, lower alkoxycarbonyl having up to 5 carbon atoms, hydroxy-lower alkoxycarbonyl having up to 5 carbon atoms, lower alkoxy-lower alkoxycarbonyl having up to 4 carbon atoms in each of the alkoxy moieties, di-lower alkylaminolower alkoxycarbonyl having up to 4 carbon atoms in each of the alkyl and alkoxy moieties, $R_3'$ represents lower alkyl having up to 4 carbon atoms or lower alkenyl having up to 4 carbon atoms, and $R_4$ and $R_5$ independently of one another, each represents hydrogen, lower alkyl having up to 4 carbon atoms, lower alkoxy having up to 4 carbon atoms, hydroxy, or halogen of an atomic number up to an including 35, or a pharmaceutically acceptable salt of a salt-forming compound of the formulae (Ib).

4. A compound according to claim 1 of the formula (II)

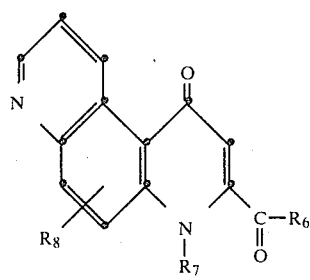

in which $R_6$ represents hydroxy or lower alkoxy having up to 4 carbon atoms, $R_7$ represents hydrogen and $R_8$ represents hydrogen or lower alkoxy having up to 4 carbon atoms, or a pharmaceutically acceptable salt of a salt-forming compound of the formula II.

5. A compound according to claim 1 of the formula (III)

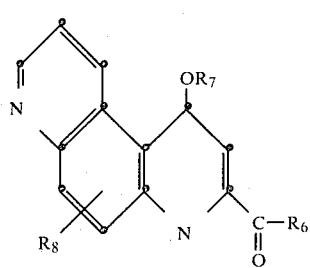

in which $R_6$ represents hydroxy or lower alkoxy having up to 4 carbon atoms, $R_7$ represents hydrogen or lower alkyl having up to 4 carbon atoms, and $R_8$ represents hydrogen or lower alkoxy having up to 4 carbon atoms, or a pharmaceuticaly acceptable salt of a salt-forming compound of the formula III.

6. A compound as claimed in claim 1 being 6-methoxy-1-oxo-1,4-dihydro-4,7-phenanthroline-3-carboxylic acid methyl ester or a pharmaceutically acceptable salt thereof.

7. A compound as claimed in claim 1 being 6-methoxy-1-oxo-1,4-dihydro-4,7-phenanthroline-3-carboxylic acid ethyl ester or a pharmaceutically acceptable salt thereof.

8. A compound as claimed in claim 1 being 6-methoxy-1-oxo-1,4-dihydro-4,7-phenanthroline-3-carboxylic acid propyl ester or a pharmaceutically acceptable salt thereof.

9. A compound as claimed in claim 1 being 6-methoxy-1-oxo-1,4-dihydro-4,7-phenanthroline-3-carboxylic acid n-butyl ester or a pharmaceutically acceptable salt thereof.

10. A compound as claimed in claim 1 being 6-n-butoxy-1-oxo-1,4-dihydro-4,7-phenanthroline-3-carboxylic acid methyl ester or a pharmaceutically acceptable salt thereof.

11. A compound as claimed in claim 1 being 6-n-butoxy-1-oxo-1,4-dihydro-4,7-phenanthroline-3-carboxylic acid n-butyl ester or a pharmaceutically acceptable salt thereof.

12. A compound as claimed in claim 1 being 1-ethoxy-6-methoxy-4,7-phenanthroline-3-carboxylic acid methyl ester or a pharmaceutically acceptable salt thereof.

13. A pharmaceutical composition useful as inhibitors of allergic reactions containing an effective amount of a compound as claimed in claim 1, together with customary pharmaceutical auxiliaries and carriers.

* * * * *

UNITED STATES PATENT AND TRADEMARK OFFICE
CERTIFICATE OF CORRECTION

PATENT NO. : 4,297,358
DATED : OCTOBER 27, 1981
INVENTOR(S) : GEORGES HAAS ET AL

It is certified that error appears in the above—identified patent and that said Letters Patent is hereby corrected as shown below:

Claim 3, Column 28, line 9 reads:

"hydroxy, or halogen of an atomic number up to an"

Should read:

-- hydroxy, or halogen of an atomic number up to and --

Signed and Sealed this

Twenty-third Day of February 1982

[SEAL]

Attest:

Attesting Officer

GERALD J. MOSSINGHOFF

Commissioner of Patents and Trademarks